US012773240B2

(12) United States Patent
Chun

(10) Patent No.: US 12,773,240 B2
(45) Date of Patent: Oct. 27, 2026

(54) RATCHET THREAD MECHANISM FOR ROD REDUCER

(71) Applicant: GLOBUS MEDICAL, INC., Audubon, PA (US)

(72) Inventor: Hayden Chun, San Diego, CA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 18/923,875

(22) Filed: Oct. 23, 2024

(65) Prior Publication Data

US 2026/0108281 A1 Apr. 23, 2026

(51) Int. Cl.
*A61B 17/70* (2006.01)

(52) U.S. Cl.
CPC ...... *A61B 17/7086* (2013.01); *A61B 17/7032* (2013.01)

(58) Field of Classification Search
CPC ........ A61B 17/7086; A61B 17/7088–17/7089; A61B 17/7083–17/7085
See application file for complete search history.

(56) References Cited

U.S. PATENT DOCUMENTS

| | | | | |
|---|---|---|---|---|
| 8,388,659 | B1 * | 3/2013 | Lab .................... | A61B 17/7082 606/267 |
| 10,085,778 | B2 | 10/2018 | Semingson et al. | |
| 10,716,602 | B2 | 7/2020 | Fischer | |
| 10,918,424 | B2 | 2/2021 | Stoll et al. | |
| 11,553,947 | B2 | 1/2023 | Park et al. | |
| 11,617,603 | B2 | 4/2023 | Wall | |
| 11,730,523 | B2 | 8/2023 | Stoll et al. | |
| 2013/0261679 | A1 * | 10/2013 | McBride .............. | A61B 17/708 606/86 A |
| 2017/0252074 | A1 * | 9/2017 | Semingson ........ | A61B 17/7091 |
| 2022/0354548 | A1 | 11/2022 | Mast et al. | |

FOREIGN PATENT DOCUMENTS

GB 2608265 A 12/2022

* cited by examiner

*Primary Examiner* — Julianna N Harvey

(57) ABSTRACT

Reduction instruments, systems, and associated methods thereof. The reduction instrument may include a housing with an internal collet positioned therein. The collet may include a compliant region defining partial split cuts, which split the body into multiple compliant members that can flex radially, and internal threads that are interrupted by the partial split cuts. A threaded reduction shaft subassembly is positioned through the collet and includes an outer threaded shaft which interacts with the internal threads of the collet. The collet is permitted to toggle between two functional states: a ratcheting position and a threading position, which allow for reduction of a spinal rod into a bone fastener.

5 Claims, 6 Drawing Sheets

RATCHET THREAD MECHANISM FOR ROD REDUCER

FIELD OF THE DISCLOSURE

The present disclosure relates to surgical instruments, and more particularly, to spinal rod reduction instruments for reducing a spinal rod into a bone fastener.

BACKGROUND OF THE DISCLOSURE

Spinal fixation constructs are utilized to provide stability and support to the spine. In a posterior fixation construct, the bone anchors (typically pedicle screws) are anchored into the pedicles of each vertebra across one or more levels of the motion segment(s). A spinal rod is connected to the bone anchors, thereby preventing motion so that fusion can occur between the vertebrae. When the position of one or more vertebrae needs to be adjusted, for example, to correct misalignments of the spinal column or restore the normal anatomical position of the vertebrae, the fixation construct also serves to maintain the new alignment until fusion is achieved.

Rod reduction instruments, for use with pedicle screw systems, utilize various mechanisms to translate the spinal rod into the bone anchor implants. Reduction instruments having a threaded shaft drive mechanism offer the benefit of superior mechanical strength to translate the rod against a high reduction load. This strength allows the instrument to forcefully translate the spinal rod toward the bone anchor, overcoming the resistance presented by the misaligned vertebrae or the tension in the surrounding tissues. Reduction instruments utilizing the threaded shaft, however, result in a slower translation to span the distance between the rod and the bone anchor. Each rotation of the shaft advances the rod only a small distance, proportional to the thread pitch. The slower movement can require significant manual effort, especially in surgeries where reduction loads are particularly high, and can lead to longer operative times. As such, there exists a need for reduction instruments that translate the rod at a faster rate of translation while still maintaining the mechanical advantage of the threaded reduction.

SUMMARY OF THE DISCLOSURE

To meet this and other needs, reduction instruments, systems, and associated methods are provided. In particular, the reduction instrument may include a ratcheting thread mechanism that allows the user to push axially on the proximal end of the threaded shaft to translate it without the need to apply a torque input. The mechanism may include a threaded collet that can radially flex in a passive, ratcheting manner. When in a ratcheting position, the reduction shaft can advance rapidly up to and against the spinal rod. The reduction instrument can then passively switch to a threading state, when a reduction load is applied by the spinal rod, to allow a torque input to further advance the threaded shaft and continue reducing the spinal rod.

According to one embodiment, a reduction instrument includes a housing defining a through bore having a stepped inner diameter, an internal collet positioned inside the through bore of the housing, and a threaded reduction shaft subassembly including an inner center shaft and an outer threaded shaft having external threads, the threaded shaft being positioned through the internal collet. The collet has a cylindrical body defining a through bore with a compliant region and a non-compliant region. The compliant region defines a plurality of partial split cuts, which split the body partially lengthwise into multiple compliant members that can flex radially. The compliant region further defines internal threads that are interrupted by the partial split cuts. The housing, internal collet, and threaded reduction shaft subassembly are aligned along a central tool axis. The internal collet is permitted to passively translate along the central tool axis between a ratcheting position and a threading position. In the ratcheting position, the external threads of the threaded shaft are permitted to ratchet over the internal threads of the collet when an axial force is applied to the threaded shaft. In the threading position, the external threads of the threaded shaft engage with the internal threads of the collet when a torque force is applied to the threaded shaft.

The reduction instrument may include one or more of the following features. The through bore of the housing may be stepped to include a proximal area having a diameter smaller than a central area of the bore. In the ratcheting position, the compliant region may be free to flex in the central area of the through bore of the housing, and in the threading position, the compliant region of the collet may be constrained by the smaller diameter of the proximal area of the through bore in the housing. The external threads of the threaded shaft may be external buttress threads that correspond with internal buttress threads in the internal collet. The buttress threads may include an asymmetric profile with an angled leading edge and a horizontal trailing edge, which permits movement in one direction while resisting movement in the opposite direction. The internal collet may have a stepped outer diameter with a narrowed proximal section, a widened distal section, and a tapered central section therebetween. The partial split cuts may extend longitudinally from the proximal section and into the tapered central section and terminate as closed circular cutouts. The compliant members may be equally spaced around a circumference of the internal collet to ensure a uniform and balanced distribution of flexion. The non-compliant region may define one or more pin slots configured to receive anti-rotation pins, which limit axial travel and rotation of the internal collet within the housing. The pin slots may extend longitudinally from an open distal end of the internal collet and terminate as a rounded closed end, which act as a stop when the internal collet translates through the housing.

According to one embodiment, a system for reducing a spinal rod includes a bone fastener having a tulip head defining a rod slot, a guide assembly releasably attachable to the tulip head of the bone fastener such that a rod slot through the guide assembly aligns with the rod slot in the tulip head, a spinal rod positionable through the rod slot in the guide assembly, and a reduction instrument attachable to the guide assembly. The reduction instrument includes a threaded reduction shaft subassembly, a housing subassembly, and an internal collet. The threaded reduction shaft subassembly includes an inner center shaft and an outer threaded shaft having external threads which engage with corresponding internal threads in the internal collet. The internal collet has a compliant region defining a plurality of partial split cuts, which split the collet partially lengthwise into multiple compliant members that can flex radially and the internal threads are interrupted by the partial split cuts. When the internal collet is in a ratcheting position, the external threads of the threaded shaft are permitted to ratchet over the internal threads of the collet when an axial force is applied to the threaded shaft to thereby translate the spinal rod along the rod slot in the guide assembly. When the internal collet is in a threading position, the external threads of the threaded shaft engage with the internal threads of the collet when a torque force is applied to the threaded shaft to thereby reduce the spinal rod into the rod slot in the bone fastener.

The system may include one or more of the following features. When in the ratcheting position, the threaded reduction shaft subassembly may be configured to advance forward without needing a torque input, thereby pushing the spinal rod distally toward the bone fastener. The housing subassembly may include a housing with spring-loaded buttons to connect the housing to the guide assembly such that the rod slot of the guide assembly aligns with the corresponding rod slot in the bone fastener for receiving the spinal rod therein. When in the ratcheting position, the compliant members of the internal collet may have clearance inside a central bore of the housing to splay radially outward and ratchet over the external threads of the threaded shaft. When the threaded reduction shaft subassembly receives a counterforce from the spinal rod, the collet may translate into the threading position, and a torque force may be applied to continue to advance the threaded reduction shaft subassembly, thereby reducing the spinal rod into the tulip head of the bone fastener. When in the threading position, the compliant members of the internal collet may not have radial clearance inside a central bore of the housing and may be constrained by the housing such that the torque force continues to reduce the spinal rod against the counterforce until the spinal rod fully seats into position in the tulip head of the bone fastener. The threaded reduction shaft subassembly may include a spring sleeve receivable on a distal portion of the inner center shaft, which is capped with a tip plunger configured for imparting a reduction force onto the spinal rod.

According to one embodiment, a method of correcting a spinal deformity may include one or more of the following steps in any suitable order: (1) anchoring a bone fastener in a vertebra, the bone fastener having a tulip head attached to a screw; (2) attaching a guide assembly having a pair of arms separated by a longitudinal slot to the tulip head of the bone fastener; (3) attaching a reduction instrument to the guide assembly, the reduction instrument having a threaded reduction shaft subassembly, a housing subassembly, and an internal collet, the threaded reduction shaft subassembly includes an inner center shaft and an outer threaded shaft having external threads which engage with corresponding internal threads in the internal collet, the internal collet has a compliant region defining a plurality of partial split cuts, which split the collet partially lengthwise into multiple compliant members that can flex radially and the internal threads are interrupted by the partial split cuts; (4) positioning a spinal rod through the slot in the guide assembly; (5) axially pushing on the threaded reduction shaft subassembly while the internal collet is in a ratcheting position such that the external threads of the threaded shaft ratchet over the internal threads of the collet to thereby translate the spinal rod along the rod slot in the guide assembly; and (6) rotationally applying a torque to the threaded reduction shaft subassembly while the internal collet is in a threading position such that the external threads of the threaded shaft engage with the internal threads of the collet to thereby continue to translate the spinal rod along the rod slot and into the tulip head of the bone fastener. The internal collet may passively move into one of two positions depending on a balance of axial forces between an applied thrust load from a user and a reduction load from the spinal rod. The method may also include locking the spinal rod within the tulip head of the bone fastener with a locking cap, and removing the guide assembly, leaving the bone fastener and spinal rod in place. The anatomy of the patient may be accessed using a standard or minimally invasive surgical (MIS) technique. The surgery may be performed with the assistance of robotic and/or navigational systems.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION OF THE INVENTION

Reduction instruments, systems, and related methods for reducing a spinal rod into a bone fastener are provided. The rod reduction instrument includes a ratcheting thread mechanism that enables two user states. In a first position or ratcheting position, the user is able to exert axial pressure on the proximal end of the threaded shaft, facilitating its translation without requiring rotational force input. In a second position or threading position, the user is able to impart a rotational torque on the threaded shaft, to drive the shaft down against the direction of the reduction load, thereby reducing the spinal rod into the bone anchor. The ratcheting thread mechanism may include a threaded collet located in the housing of the reduction instrument. The threaded collet may include compliant and non-compliant regions, which allows the collet to switch between states when it translates along the housing. In this manner, the collet is permitted to translate into two different positions, thereby triggering one of the two user states, to behave either as a ratchet or a threaded nut. The collet may passively translate into these two positions depending on the balance of axial forces between the applied thrust load from the user and the reduction load from the spinal rod.

Figure 1:
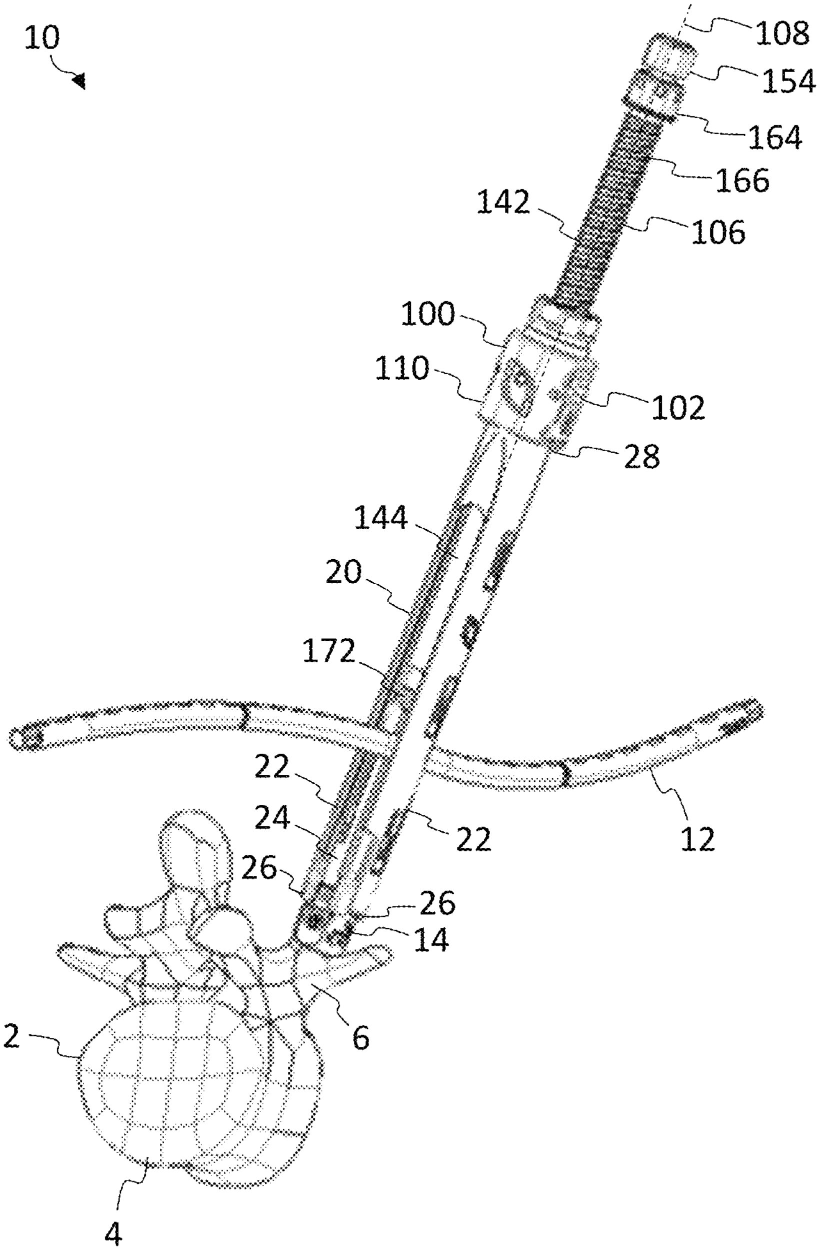
FIG. 1 shows a perspective view of a rod reduction instrument configured for translating or reducing a spinal rod into a bone fastener attached to the pedicle of a vertebra according to one embodiment.

Turning now to the figures, where like reference numbers may refer to like elements, FIG. 1 shows a perspective view of a rod reduction system 10 including a reduction instrument 100 configured for reducing a spinal rod 12 into a bone fastener 14, such as a pedicle screw, attached to a vertebra 2. Generally speaking, the reduction instrument 100 is used to fully seat or reduce the spinal rod 12 into the bone fastener 14 and thereafter insert a locking cap to secure the spinal rod 12 therein. The reduction instrument 100 translates the spinal rod 12 toward the bone fastener 14, overcoming the resistance presented by the misaligned vertebrae or the tension in the surrounding tissues. Although only a single vertebra 2 is shown, similar reductions may occur bilaterally or at other levels to complete the posterior fixation construct. The reductions may help to correct misalignments caused by conditions, such as scoliosis, kyphosis, lordosis, or cases of trauma or spondylolisthesis. The reduction instrument 100 ensures that the spinal rod 12 is properly seated in the bone fastener 14, thereby achieving optimal spinal alignment and restoring the biomechanical integrity of the spine.

During spinal surgery, one or more bone fasteners 14 may be anchored into respective vertebrae 2. The bone fasteners 14 may be installed during a minimally invasive surgical (MIS) procedure, for example, such that the bone fastener 14 is positioned through a guide tube or cannula to access and guide the bone fastener 14 into the vertebra 2. Alternatively, the bone fasteners 14 may be installed in an open or semi-open approach to the spine. The surgery may also be performed with the assistance of robotic and/or navigational systems.

In this embodiment, the bone fastener 14 includes a pedicle screw anchored into the pedicle 6 of the vertebra 2, which are small bony structures connecting the vertebral body 4 to the facet joints in the spine. Although only one bone fastener 14 is shown, it will be appreciated that the posterior fixation construct may include a unilateral or bilateral application of pedicle screws 14 into one or more vertebra across one or more levels of the spine. The pedicle screws 14 create solid anchor points for the spinal rod 12. The final fixation construct helps to provide correction, facilitate the fusion process, and offer stability to the spine.

The bone fastener 14 may include a bone screw, anchor, clamp, or the like configured to engage bone. The bone fastener 14 may include a bone screw having a screw head connected to a threaded shaft, and a tulip head or tulip head assembly attachable to the bone screw. While the screw head may have any general shape, in the case of a polyaxial fastener, at least a portion of the screw head may have a curved surface in order to allow for rotational movement and/or angular adjustment of the bone screw with respect to a tulip head. For example, at least a portion of the screw head may be shaped to form a portion of a ball or at least a portion of a sphere. The screw head may be smooth, threaded, provided with a roughened or textured surface, or may be otherwise configured to interface with the tulip head assembly. The screw head may have a tool engagement surface or drive recess, such as a hexalobular recess, that can be engaged, for example, by a screw-driving instrument or other device. It will be appreciated that any suitably shaped tool engagement surface may be provided.

The threaded bone screw includes one or more bone threads configured to engage bone. The bone threads include external helical ridges that follow a helical path around the periphery of the shank, which are configured for anchoring the bone fastener 14 into bone. Varying bone thread forms may be used, such as corticocancellous, dual outer diameter (DOD), or cortical (e.g., midline cortical screw or MCS). The bone threads may include a single lead with one continuous thread that spirals around the screw's body, dual lead threads with two separate leads, or other variations, such as triple lead threads, variable pitch threads, fluted threads, etc. The threaded shaft may have a number of different features, such as thread pitch, shaft diameter to thread diameter, overall shaft shape, and the like, depending, for example, on the particular application. The designs may be tailored to meet specific biomechanical needs, optimize bone healing, enhance surgical outcomes, and reduce insertion times, for example. Cannulations and fenestrations may also be employed for placement over a guide wire or k-wire and/or for delivery of bone cement.

The bone fastener 14 may include a tulip head or tulip head assembly attachable to the bone screw. The tulip head includes opposed arms defining a U-shaped channel or rod slot sized and configured to accept the spinal rod 12. Each of the arms may have interior threaded portions or other mechanisms for engaging the locking cap such that the spinal rod 12 may be secured in the tulip head with the locking cap. The bone fastener 14 may be included in an assembly with pre-assembled tulip heads of varying styles, or as a modular component where a modular head assembly is attached to the bone screw intraoperatively. For a polyaxial implant, the tulip head assembly may permit polyaxial movement relative to the bone screw, and tightening the locking cap compresses the rod 12 into the tulip head, thereby restricting motion of the bone fastener 14 and forming a rigid construct. In addition to polyaxial tulip head styles, it will be appreciated that any suitable tulip type may be selected including unilateral, monoaxial, fixed, etc., which offer different degrees of flexibility, stability, and ease of use based on the requirements of the spinal procedure. Examples of bone fasteners, other implants, and rod constructs are described in more detail, for example, in U.S. Pat. No. 10,368,917, which is incorporated by reference herein in its entirety for all purposes.

Once the bone fastener 14 is anchored to the pedicle 6, the spinal rod 12 may be secured in the tulip head of the bone fastener 14. The spinal rods 12 may be used to stabilize the spine, correct deformities, and maintain proper alignment of the spine. The spinal rod 12 may be an elongated shaft having a generally cylindrical outer body. It will be appreciated that the spinal rod 12 may also have other suitable cross-sectional shapes, such as oval, rectangular, or flattened surfaces. The rod 12 may be made from biocompatible materials, such as titanium, titanium alloys, cobalt-chrome alloys, or stainless steel, that have high tensile strength and can withstand forces and stresses placed on the spine. The choice of rod type, size, and material may be influenced by the specific surgical goals, the patient's anatomy, and the surgeon's preference. During the surgery, the surgeon may need to bend the rod 12 to match the patient's spinal curvature, to align with new or existing hardware, such as screw or tulip heads, and/or to achieve the desired correction when corrective forces are applied to the rod 12. In surgeries for conditions like scoliosis or kyphosis, the rods 12 may be bent to correct abnormal curvatures, to realign the spine, and to act as a brace to maintain the spine in its new corrected position. In stabilization procedures, the rods 12 provide the necessary stability to the affected segments of the spine. For spinal fusion, the rods 12 help to maintain proper alignment of the spine while the vertebrae fuse together.

The spinal rod 12 may be reduced or seated into the tulip head of the bone fastener 14 by the reduction instrument 100. The reduction instrument 100 may work with an extension guide or guide assembly 20 that aligns with the rod slot in the tulip head to help direct the rod 12 into the tulip head of the bone fastener 14. The guide assembly 20 may include an outer tube or a pair of arm members 22 that define a rod slot 24 therebetween. The distal ends 26 of the arm members 22 may releasably attach to the top or sides of the tulip head of the bone fastener 14. Alternatively, the guide assembly 20 may include integral break-off extension guides, which are integrally formed with the tulip head and may break off from the bone fastener 14 after use. It will be appreciated that any suitable type of guide assembly or extensions may be selected. The rod slot 24 between arms members 22 define an enclosed guide channel which is dimensioned to allow passage of the spinal rod 12 as it is translated distally into the tulip head of the bone fastener 14. The proximal end 28 of the guide assembly 20 may be configured to connect or attach to the reduction instrument 100, which translates the spinal rod 12. Further details on suitable guide assemblies or rod reduction instruments are further provided in U.S. Pat. Nos. 11,723,698 and 11,766,281, which are incorporated by reference herein in their entireties for all purposes.

Figure 2:
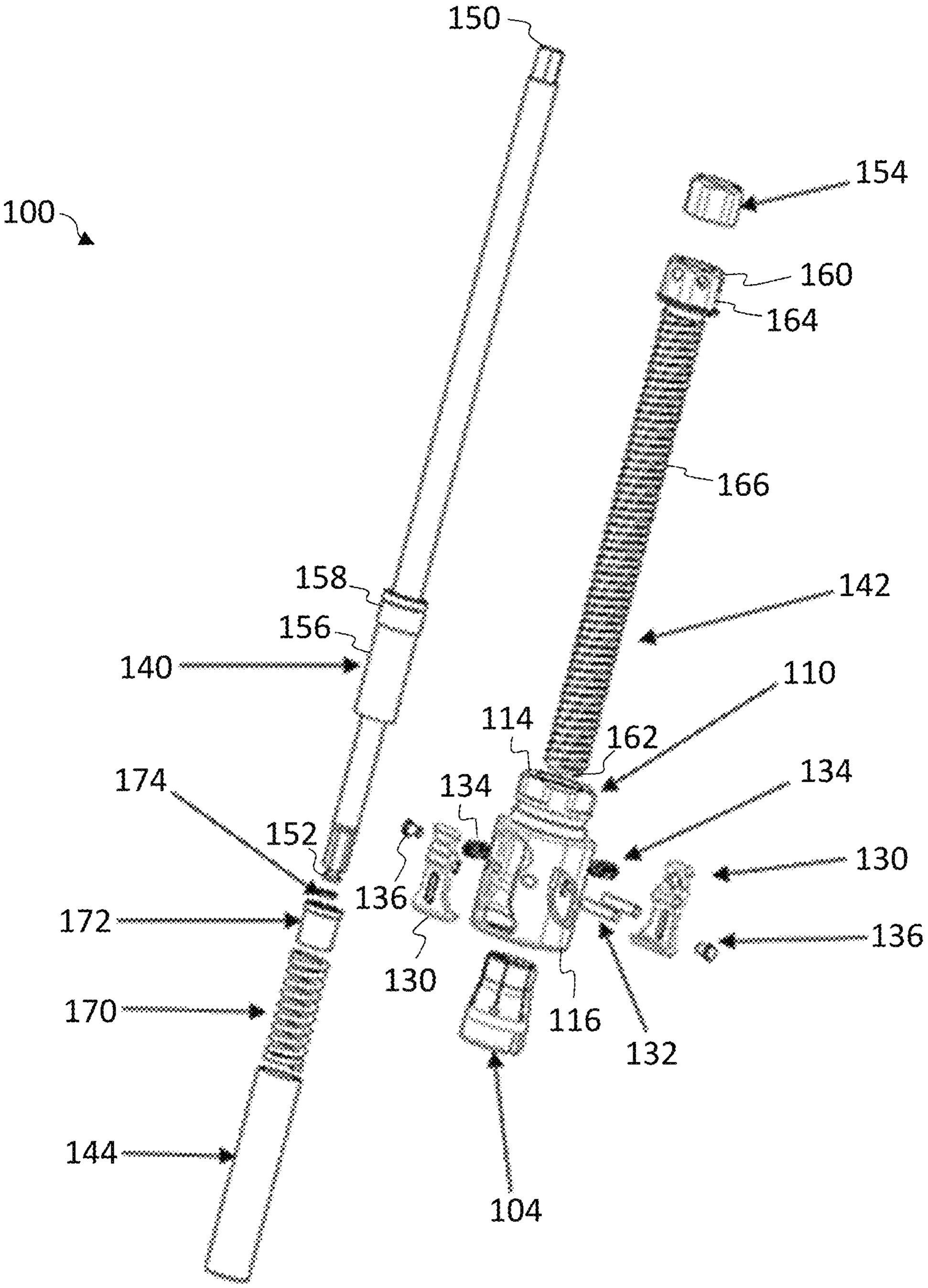
FIG. 2 shows an exploded view of the rod reduction instrument including a housing subassembly receiving a threaded collet, which interacts with a threaded reduction shaft subassembly in a ratcheting or threading manner to reduce the spinal rod according to one embodiment.

As best seen in FIG. 2, the reduction instrument 100 includes a housing subassembly 102 for retaining a threaded collet 104 and a threaded reduction shaft subassembly 106 for pushing the spinal rod 12 distally along the guide assembly 20. The housing subassembly 102, internal threaded collet 104, and threaded reduction shaft subassembly 106 are aligned along a central longitudinal instrument axis 108. The housing subassembly 102 attaches the reduction instrument 100 to the guide assembly 20 and retains the threaded collet 104 in two discrete positions configured for moving the threaded reduction shaft subassembly 106 in axial or rotational manners, respectively.

The housing subassembly 102 includes a primary housing component 110, pins 136 for limiting axial travel and rotation of the collet 104 within the housing 110, and a set of buttons 130, pins 132, and springs 134 for engaging with mating tulip head extensions or guide assemblies, such as guide assembly 20. In particular, the primary housing component 110 includes a connector or housing that releasably couples the reduction instrument 100 to the guide assembly 20.

Figure 4A:
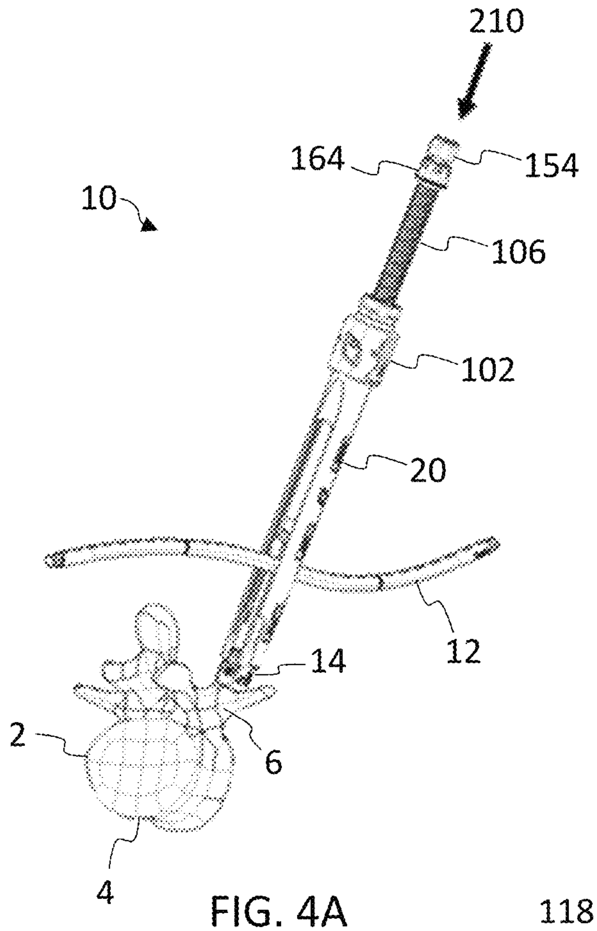
FIGS. 4A-4B show an axial force applied to translate the threaded shaft of the rod reduction instrument for rapid reduction of the spinal rod, and a close-up cross-sectional view of the threaded collet in the ratchet position such that the collet permits the threaded shaft to ratchet distally forward for rapid reduction according to one embodiment.
Figure 4B:
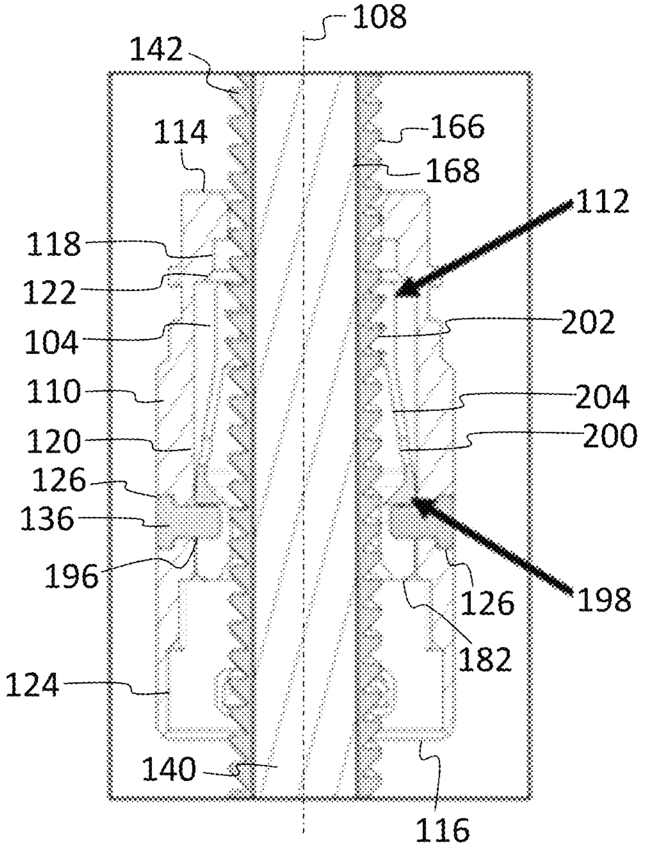
Figure 5A:
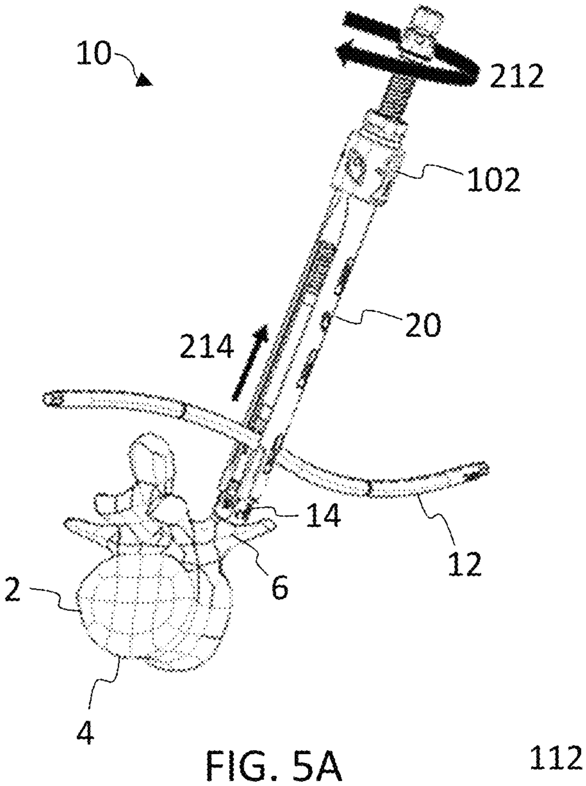
FIGS. 5A-5B show a torque applied to the threaded shaft of the rod reduction instrument to continue reducing the spinal rod against the reduction load, and a close-up cross-sectional view of the threaded collet in the threading position such that the collet permits the threaded shaft to rotate to drive the shaft down against the direction of the reduction load, thereby reducing the spinal rod into the bone fastener according to one embodiment.
Figure 5B:
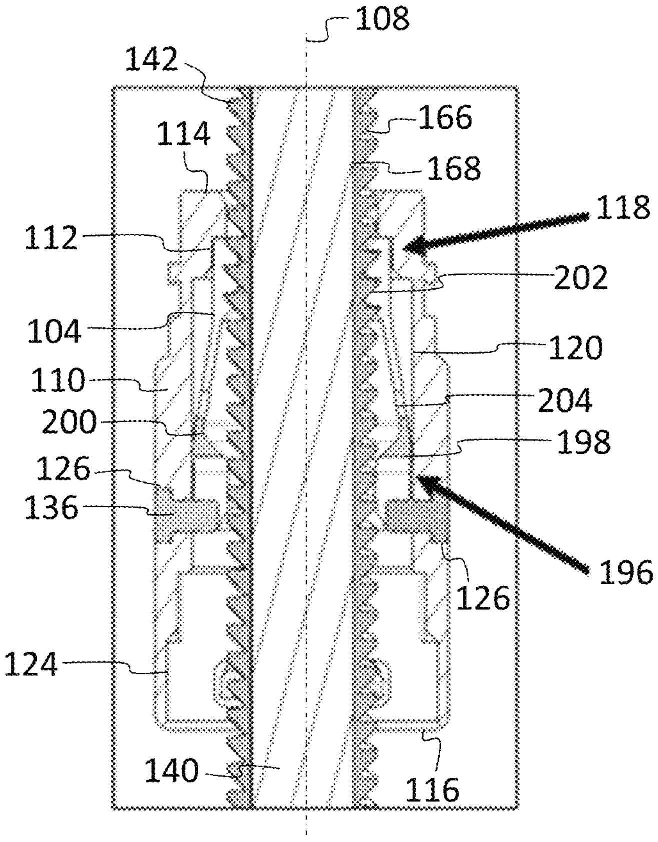

The housing 110 may have a generally cylindrical body defining an internal cavity 112. The internal cavity 112 may include a through bore extending from a proximal end 114 to a distal end 116 of the housing 110. The internal cavity 112 is sized and dimensioned to receive the threaded collet 104 therein and the threaded reduction shaft subassembly 106 therethrough. As best seen in FIGS. 4B and 5B, the internal cavity 112 may include a stepped bore including a proximal area 118 having a diameter or dimensions smaller than a central area 120. The transition 122 between the proximal and central sections 118, 120 of the bore 112 may include an angled or sloped transition from the narrower section 118 to the wider section 120. A distal section 124 of the bore 112 may be sized and dimensioned to retain the proximal end 28 of the guide assembly 20, thereby securing the guide assembly 20 to the housing 110.

The housing 110 further defines one or more holes, openings, or recesses configured to receive one or more buttons 130, pins 132, springs 134, or the like. In particular, the housing 110 may define one or more pin holes 126 configured for receiving corresponding anti-rotation pins 136. The anti-rotation pins 136 prevent rotation of the collet 104 and act as a stop when the collet 104 translates downward within the cavity 112 in the housing 110. The pin holes 126 may include a pair of transverse bores, which are generally perpendicular to the instrument axis 108.

The housing subassembly 102 may further include a pair of spring-loaded clips or buttons 130 that connect the housing 110 to the guide assembly 20. The buttons 130 may be retained by button pins 132, such as cylindrical dowels, that hold the buttons 130 in place within the housing 110. The buttons 130 may be spring-loaded via springs 134, which provide the necessary force to keep the buttons 130 engaged with the guide assembly 20 until released. The spring action ensures that the buttons 130 remain in their default position to maintain a secure attachment. The spring-loaded buttons 130 facilitate quick and secure attachment or detachment of the housing 110 to the guide assembly 20. The user can easily press these buttons 130 to disengage the clips from the guide assembly 20. Any other suitable attachment mechanism may also be used to temporarily secure the housing 110 to the guide assembly 20.

The housing 110 retains the threaded collet 104 and the internal threaded reduction shaft subassembly 106. The threaded reduction shaft subassembly 106 has a torque driver 164 on the proximal end 150 for torque input and axial loading, an external buttress thread geometry 166, and a distal end 152 designed to engage with the locking cap and to push against the spinal rod 12 for reduction. The threaded reduction shaft subassembly 106 may advance rapidly with axial force in the ratcheting state and advance deliberately with torque force in the threading state against the spinal rod 12 to reduce the spinal rod 12 into the bone fastener 14.

The threaded shaft subassembly 106 may include an inner center shaft 140, an outer threaded shaft 142, and an outer spring sleeve 144. The center shaft 140 may include a cylindrical rod that extends from a proximal end 150 to a distal end 152. The proximal end 150 of the inner shaft 140 may be configured to receive a drive part 154, such as a hex drive, which rotates the inner shaft 140, for example, for installation of the locking cap. The distal end 152 of the inner shaft 140 may include a distal tip, for example, configured to engage with a drive recess in the locking cap. The inner shaft 140 may include an enlarged shaft portion 156 that defines a shoulder 158 separating a proximal portion of the shaft 140 for retaining the threaded shaft 142 from a distal portion of the shaft 140 for retaining the spring sleeve 144.

The threaded shaft 142 may include an elongated and cylindrical shaft extending from a proximal end 160 to a distal end 162. The proximal end 160 may include a drive nut 164, which may impart a torque to the threaded shaft 142 when rotated. The drive nut 164 may have a geometric shape, like a hexagon, that interfaces with corresponding tools for driving or turning the shaft 142. The length of the threaded shaft 142 may include one or more external threads 166 configured to engage with corresponding threads 202 inside threaded collet 104. The external threads 166 may include buttress threads, which act as a ratcheting mechanism or a threading mechanism when the external threads 166 interface with the internal threads 202 of the collet 104. The buttress threads 166 may include a sloped or angled leading edge and a steep or almost horizontal trailing edge. This asymmetrical profile allows for ratcheting movement in one direction (e.g., axial movement in the distal direction) while resisting motion in the opposite direction (e.g., in the proximal direction). Although a buttress thread is exemplified it will be appreciated that other types of threads, ratcheting teeth, or other mechanisms may be employed to interact with the collet 104 to impart the ratcheting and torque conditions. The threaded shaft 142 further defines a hollow bore 168 along the central tool axis 108. The through bore 168 may be sized and dimensioned to receive the proximal portion of the center shaft 140 therethrough, and impart axial movement to the threaded reduction shaft subassembly 106.

The spring sleeve 144 may include a hollow tube or cylindrical casing receivable on the distal portion of the center shaft 140. The spring sleeve 144 may include a spring 170 positioned within the spring sleeve 144 configured to exert a force along the axis of the sleeve 144. The spring sleeve 144 may be capped with a tip plunger 172, which acts as the functional endpoint of the reduction shaft subassembly 106 when imparting a reduction force on the spinal rod 12. A retention clip 174 may be used to retain the tip plunger 172 and spring sleeve 144 on the center shaft 140. The distal tip 152 may be configured to extend through the tip plunger 172, following the reduction of the spinal rod 12 into the bone fastener 14, to install and secure the locking cap.

Figure 3A:
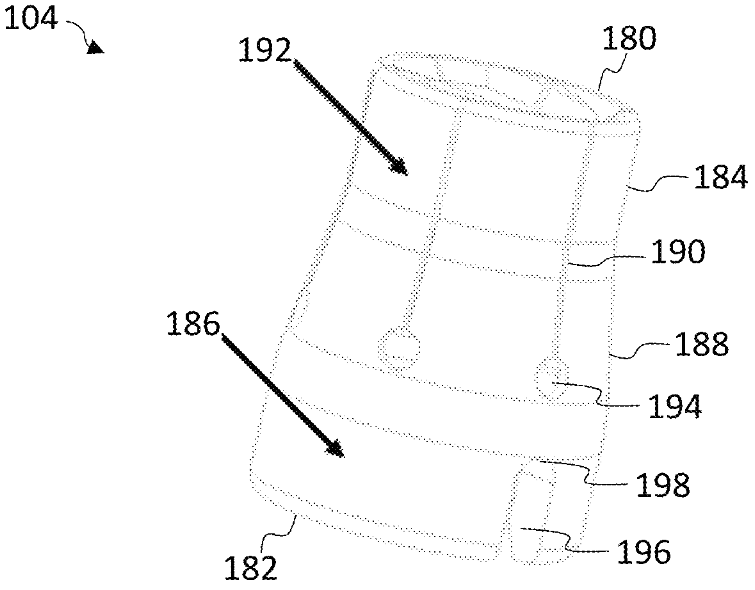
FIGS. 3A-3B show perspective and cross-sectional views, respectively, of the threaded collet according to one embodiment.
Figure 3B:
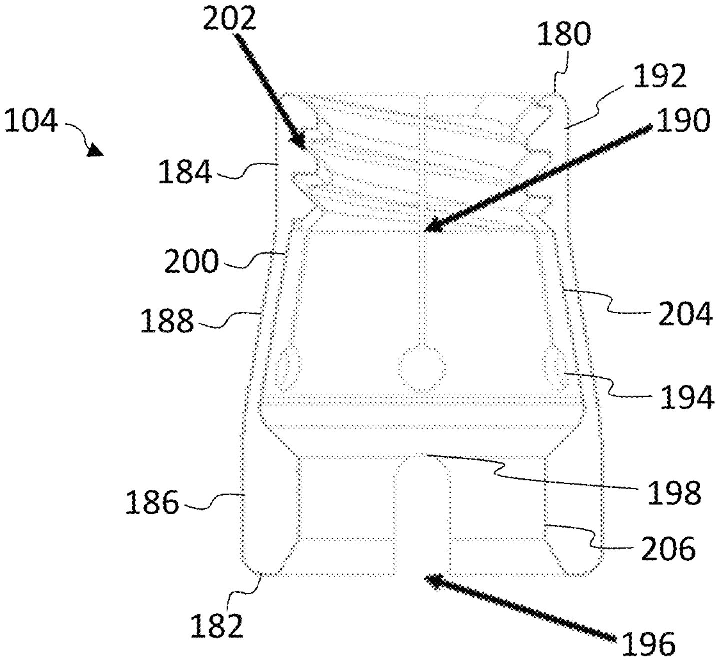

With further emphasis on FIGS. 3A-3B, the threaded collet 104 is shown in further detail. The threaded collet 104 has multiple compliant zones 192, internal buttress threads 202, and pin slots 196 for limiting axial travel of the collet 104 within the housing 110. The threaded nut collet 104 is positioned inside the internal cavity 120 of the housing 110 and is constrained by the collet anti-rotation pins 136, which pass through pinholes on the housing 110 and through pin slots 196 on the collet 104. The threaded shaft 142 is positioned inside of the collet 104, and the center shaft subassembly components 106 are assembled inside the cannulation 168 of the threaded shaft 166.

The collet 104 includes a cylindrical body extending from a proximal end 180 to a distal end 182. The collet 104 may be characterized by a general cylindrical shape with a stepped outer diameter. The collet 104 may include a narrowed proximal section 184, a widened distal section 186, and a tapered central section 188 therebetween. In other words, the narrowed proximal section 184 may have an outer diameter smaller than the outer diameter of the widened distal section 186. The central section 188 may be tapered from the narrowed proximal section 184 to the widened distal section 186.

The proximal section 184 may form a compliant section or region of the collet 104. The proximal section 184 and/or tapered section 188 of the collet 104 define multiple partial cuts 190 from the proximal end 180, which split the part partially lengthwise. The partial cuts 190 may include slits, slots, or splits that define multiple compliant members 192. Each cut 190 effectively turns the intervening material between the cuts 190 into the compliant members 192. The cuts 190 may extend longitudinally from the open proximal end 180 and into the tapered section 188. Each slit 190 may terminate as a round or circular cutout 194, for example. These splits 190 allow the proximal portion 184 of the collet 104 to flex or bend radially in a compliant fashion. The compliant members 192 may be equally spaced around the circumference of the collet 104 to ensure a uniform and balanced distribution of flexion. It will be appreciated that any suitable number of slits 190, resulting compliant members 192, and their locations or orientation may be selected for the desired flexion or bending of the resulting compliant members 192 of the collet 104.

The distal section 186 may form a non-compliant section of the collet 104. The non-compliant section 186 may be rigid and resistant against deformation. The distal section 186 may include a thickened or reinforced wall thickness configured to withstand greater mechanical forces and prevent flexion or bending. The collet 104 may define one or more pin slots 196 that pass through the non-compliant region 186. The pins slots 196 may include anti-rotation pin slots configured to receive at least a portion of the corresponding anti-rotation pins 136. The pin slots 196 may extend longitudinally from the open distal end 182 and into the distal section 186 terminating at a closed end 198. The closed end 198 may be rounded or semi-circular, which may function as a stop when the collet 104 translates through the housing 110. A pair of opposed pin slots 196 may be provided on opposite sides of the distal section 186 to receive two respective anti-rotation pins 136.

The collet 104 defines an internal cavity or through bore 200 along the center axis 108 from the proximal end 180 to the distal end 182 of the collet 104. A proximal portion of the bore 200 defines internal threads 202 configured to interact with corresponding external threads 166 on the threaded shaft 142. The internal threads 202 may extend through the narrowed proximal section 184 of the collet 104. The compliant members 192 may define the internal threads 202, which are interrupted by the split cuts 190. In one embodiment, the compliant members 192 have internal buttress threads 202 that are interrupted by the split cuts 190. The internal buttress threads 202 may mimic the geometry of the external buttress threads 166 on the threaded shaft 142. A central portion of the bore 200 may define an internal taper 204, which mimics the tapered outer shape of the tapered section 188. A distal portion of the bore 200 may define a stepped area 206 that narrows to approximately the outer diameter of the threaded shaft 142 while providing clearance therethrough.

The collet 104 sits inside the internal stepped bore 112 of the housing 110. The non-compliant distal region 186 of the collet 104 sits within the bore 112 of the housing 110, coaxially constraining the part. The set of anti-rotation pins 136 may be oriented radially around the center axis 108 of the housing 110 and pass through the housing 110 and into the pin slots 196 of the collet 104. Together, these pins 136 and the stepped bore 112 of the housing 110 limits the range of axial travel of the collet 104 within the housing 110. The pins 136 serve another function to prevent axial rotation of the collet 104 within the housing 110. The anti-rotation function can also come in the form of alternative embodiments, such as a flat face on the outer diameter of the non-compliant region, mating flat geometry on the internal bore of the housing, or other suitable arrangements.

The collet 104 translates inside the housing 110 along axis 108 into the two functional states. In a first state, the collet 104 functions as a ratchet mechanism when an axial force 210 is applied to the threaded reduction shaft subassembly 106. In a second state, the collet 104 functions as a torque mechanism whereby a torque force 212 is applied to the threaded reduction shaft subassembly 106 to continue reducing the spinal rod 12. As shown in FIGS. 4A-4B, when the axial force 210 is imparted to threaded shaft 142, the collet 104 is translated distally into the center bore 120 of the housing 110. In this position, the threaded collet 104 can radially flex in a passive, ratcheting manner. This allows the threaded reduction shaft 142 to advance forward without needing a torque input. As shown in FIGS. 5A-5B, when a counter force 214 is applied to the collet 104 from the spinal rod 12, the collet 104 is translated proximally and into the proximal bore 118 of the housing 110. When the shaft 142 is pushed against the reduction load 214 from the spinal rod 12, the threaded collet 104 is no longer compliant and behaves like a traditional threaded nut. The user can then apply torque input 212 on the threaded shaft 142 to continue to translate the center shaft 140 distally, thereby reducing the spinal rod 12 into the bone fastener 14. In other words, the reduction load 214 passively switches the state of the collet 104 to allow for the torque input 212 to further advance the threaded reduction shaft subassembly 106 towards the bone fastener 14.

The threaded reduction shaft subassembly 106 sits along the center axis 108 of the part, passing through the bore 112 of the housing 110 and the center bore 200 of the collet 104. In alternative embodiments, the translational range of the collet 104 can be limited entirely by steps in the internal bore 112 of the housing 110, entirely by a set of pins and pin slots, retention rings in a groove of the housing bore, or other suitable mechanisms.

Figure 6A:
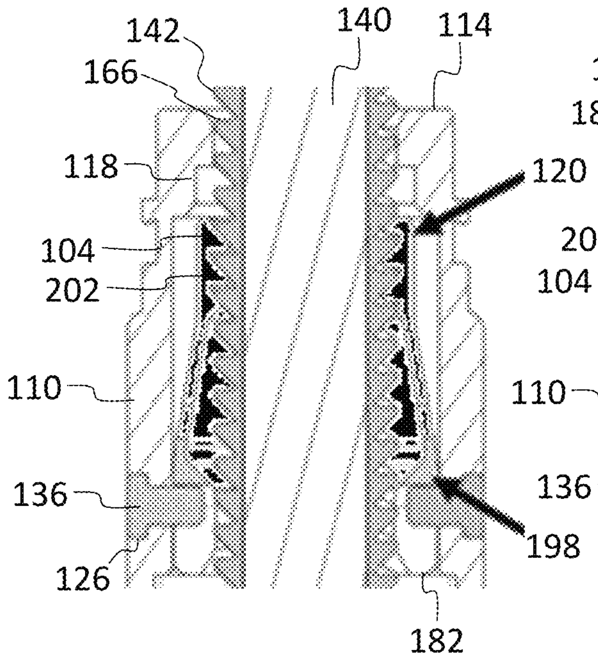
FIGS. 6A-6B show side-by-side cross-sectional comparisons of the positioning of the threaded collet within the housing assembly for ratcheting and threading states, respectively.
Figure 6B:
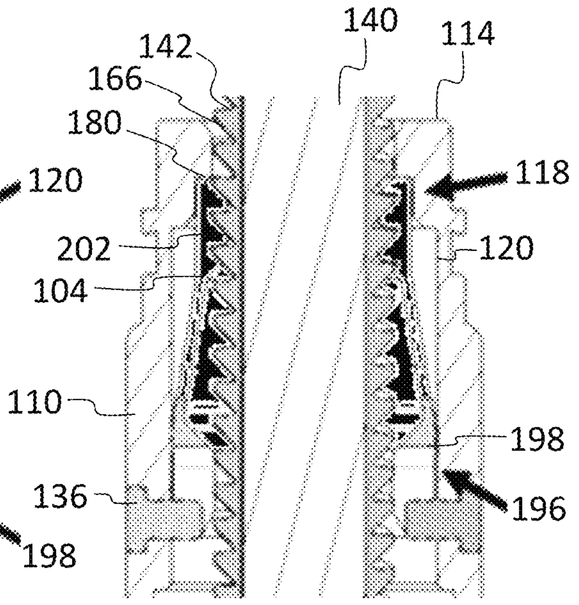

With further emphasis on FIGS. 6A-6B, the collet 104 is configured to exhibit a dual-state functionality depending on its position in the housing 110. The collet 104 can behave either as a compliant ratchet (FIG. 6A) or as a threaded nut (FIG. 6B), depending on its axial position within the housing 110. As shown in FIG. 6A, when the thrust load 210 is applied by the user on the proximal end 160 of the threaded shaft 142, the load 210 translates the collet 104 distally within the housing 110. The collet 104 reaches the end of its axial travel when the pins 136 reach the end 198 of the collet pin slots 196, also known as the ratcheting position. When the collet 104 is in its ratcheting position, the clearance between the outer diameter of its compliant members 192 and the internal bore 120 of the housing 110 is greater than the difference between the major diameter and the minor diameter of the buttress threads 166. The angled faces of the buttress thread-form act as ramps, transmitting an axial thrust load on the threaded shaft 142 into a radial force that elastically deforms the compliant members 192 away from the threaded shaft 142. The compliant members 192 may function essentially as pawls of a ratchet and snap back into place into the next set of threads. The collet 104 continues to ratchet over the threads 166 of the shaft 142 as the user continues to apply the thrust load 210. The compliant members 192 do not plastically deform in the ratcheting action. In this manner, the shaft 140 may be manually advanced without applying any torque to the threaded shaft 142. This allows the user to rapidly advance the threaded reduction shaft subassembly 106 and into contact the spinal rod 12.

As shown in FIG. 6B, once the distal tip 172 of the reduction shaft 140 reaches the spinal rod 12 and continues to advance forward, the opposing reduction load 214 of the spinal rod 12 pushes against the distal end 152 of the reduction shaft like a leaf spring. The flat faces of the buttress thread-form bear the reduction load from the spinal rod 12 and prevent the shaft 142 from ratcheting in the opposite direction. When the user-applied thrust load 210 is released, the reduction load 212 from the spinal rod 12 translates the collet 104 proximally. When the collet 104 tops out on the proximal step 118 inside the housing 110, the collet 104 is in its threading position. The translation of the collet 104 into the threading position occurs passively and does not need a secondary input from the user to move it into position. In the threading position, there is reduced diametric clearance between the outer diameter of the collet's compliant members 192 and the counterbore 118 of the housing 110. This reduced clearance is less than or equal to the difference between the major diameter and minor diameter of the buttress threads 166. As a result, the compliant members 192 are limited in their ability to flex radially outwards. The collet 104 can no longer passively ratchet and behaves like a traditional threaded nut. The user may now apply torque 212 on the proximal drive 164 of the threaded shaft 142 to continue advancing the threaded reduction shaft subassembly 106 against the reduction load 214 to seat the spinal rod 12 in the bone fastener 14. The pins 136 in the pin slots 196 ensure that the collet 104 remains clocked with the housing 110 so that it does not rotate as the shaft 142 is torqued. The instrument 100 can be reset by applying a counterclockwise torque on the proximal drive 164 of the shaft 142 to retract the threaded shaft 142.

One example of a method of reduction is described below, which may include one or more of the following steps in any suitable order. First, a posterior portion of the spine may be accessed, for example, in a minimally invasive approach. The surgery may be performed with the assistance of robotic and/or navigational systems. A spinal bone fastener 14, such as a pedicle screw, may be anchored through the pedicle 6 of each vertebra 2 to be fixated. The pedicle screws 14 may be inserted bilaterally or unilaterally into vertebrae 2 across one or more levels. With the pedicle screws 14 in position, spinal rod 12 may be selected and sized to span the screws 14 and optionally bent or contoured. When the spinal rod 12 is in need of reduction to seat the spinal rod 12 into the tulip head of the pedicle screw(s) 14 (e.g., in the case where the vertebrae are misaligned), the reduction instrument 100 may be used on one or more of the levels. In each instance where reduction is needed, the guide assembly 20 may be attached to the tulip head of the pedicle screw 14. The reduction instrument 100 may be attached to the proximal end 28 of the guide assembly 20, for example, by positioning its end within the housing 110 and allowing the spring-loaded buttons 130 to facilitate quick and secure attachment of the housing 110 to the guide assembly 20. The spinal rod 12 is positioned through the rod slot 24 of the guide assembly 20. Next, an axial force 210 is applied to the proximal end 150 of the reduction shaft subassembly 106 (e.g., onto hex drive 154). The collet 104 is translated forward into the central bore 120 of the housing 110. Until a reduction load 214 is met, the reduction shaft subassembly 106 quickly translates distally by ratcheting through collet 104. In the ratcheting position, the compliant members 192 of the collet 104 have clearance inside the central bore 120 of the housing 110 to splay radially outward and ratchet over the threads 166 of the threaded shaft 142 (e.g., the clearance is greater than the major diameter and minor diameter of the threaded shaft 142). Once the tip plunger 172 contacts the spinal rod 12 and the counter reduction load 214 is encountered, the collet 104 is then translated backward into the proximal bore 118 and enters the threading position. In the threading position, the compliant members 192 do not have radial clearance to ratchet over the thread height (e.g., the clearance is less than or equal to the major diameter and minor diameter of the threaded shaft 142). Instead, when torque 212 is applied on hex drive 164 at the proximal end 160 of the threaded shaft 142, the tip plunger 172 continues to reduce the spinal rod 12 against the reduction load 214 until the rod 12 fully seats into position in the tulip head of the bone fastener 14. The reduction may correct misalignments, restore the anatomical position of the vertebrae, and/or adjust the spinal curvature to a more natural alignment. Once the spinal rod 12 is fully seated, a locking cap can be secured using the distal tip 152 of the center shaft 140, by rotating drive nut 154 and rotating center shaft 140, thereby fully locking the spinal rod 12 in the bone fastener 14. Reduction and locking cap engagement may be completed for each pedicle screw 14 in the construct. Once complete, the guide assembly 20 and instrument 100 can be removed from the screw(s) 14, and the incisions can be closed. The reductions ensure that the spinal rod(s) 12 and screw(s) 14 are optimally positioned to bear loads and support spinal movement. A successful reduction increases the likelihood of achieving the surgical goals, such as solid fusion and permanent stability of the spine.

The reduction instrument 100 and ratcheting thread mechanism may offer one or more advantages. First, the interrupted buttress threads 202 in the compliant members 192 of the collet 104 allow the collet 104 to toggle between two functional conditions. The angled, ramped portion of the threads 202 allow the compliant members 104 to ratchet when the reduction shaft 106 is thrusted in the forward direction or direction of reduction. The flats of the buttress threads 202 prevents ratcheting in the backwards direction from the reduction load 214 from the spinal rod 12. Second, the pin slots 196 of the collet 104 and stepped internal bore 112 of the housing 110 limit rotation of the collet 104 inside of the housing 110 and set hard limits on the allowable axial translation of the collet 104. Third, the collet 104 has the ability to translate into two different positions to thereby behave either as a ratchet or as a threaded nut. Fourth, the instrument 100 is able to passively translate the collet 104 into its two positions depending on the balance of axial forces between the applied thrust load 210 from the user and the reduction load 214 from the spinal rod 12.

It will be further understood that various changes in the details, materials, and arrangements of the parts which have been described and illustrated in order to explain the nature of this invention may be made by those skilled in the art without departing from the scope of the invention as expressed in the claims. One skilled in the art will appreciate that the embodiments discussed above are non-limiting. It will also be appreciated that one or more features of one embodiment may be partially or fully incorporated into one or more other embodiments described herein.

The invention claimed is:

1. A system for reducing a spinal rod comprising:

a bone fastener having a tulip head defining a rod slot;

a guide assembly releasably attachable to the tulip head of the bone fastener such that a rod slot through the guide assembly aligns with the rod slot in the tulip head;

a spinal rod positionable through the rod slot in the guide assembly; and a reduction instrument attachable to the guide assembly, the reduction instrument including a threaded reduction shaft subassembly, a housing subassembly, and an internal collet, the threaded reduction shaft subassembly includes an inner center shaft and an outer threaded shaft having external threads which engage with corresponding internal threads in the internal collet, the internal collet has a compliant region defining a plurality of partial split cuts, which split the collet partially lengthwise into multiple compliant members that can flex radially and the internal threads are interrupted by the partial split cuts, wherein when the internal collet is in a ratcheting position, the external threads of the threaded shaft are permitted to ratchet over the internal threads of the collet when an axial force is applied to the threaded shaft to thereby translate the spinal rod along the rod slot in the guide assembly, and when the internal collet is in a threading position, the external threads of the threaded shaft engage with the internal threads of the collet when a torque force is applied to the threaded shaft to thereby reduce the spinal rod into the rod slot in the bone fastener, wherein the housing subassembly includes a housing with spring-loaded buttons to connect the housing to the guide assembly, and wherein when the threaded reduction shaft subassembly receives a counterforce from the spinal rod, the collet translates into the threading position, and the torque force is applied to continue to advance the threaded reduction shaft subassembly, thereby reducing the spinal rod into the tulip head of the bone fastener.

2. The system of claim 1, wherein when in the ratcheting position, the threaded reduction shaft subassembly is configured to advance forward without needing a torque input, thereby pushing the spinal rod distally toward the bone fastener.

3. The system of claim 1, wherein when in the ratcheting position, the compliant members of the internal collet have clearance inside a central bore of the housing to splay radially outward and ratchet over the external threads of the threaded shaft.

4. The system of claim 1, wherein when in the threading position, the compliant members of the internal collet do not have radial clearance inside a central bore of the housing and are constrained by the housing such that the torque force continues to reduce the spinal rod against the counterforce until the spinal rod fully seats into position in the tulip head of the bone fastener.

5. The system of claim 1, wherein the threaded reduction shaft subassembly includes a spring sleeve receivable on a distal portion of the inner center shaft, which is capped with a tip plunger configured for imparting a reduction force onto the spinal rod.

* * * * *